(12) United States Patent
Takahashi et al.

(10) Patent No.: US 9,181,177 B2
(45) Date of Patent: Nov. 10, 2015

(54) METHOD OF PRODUCING CYCLOALKANONE OXIME

(75) Inventors: Toru Takahashi, Nagoya (JP); Yasuyoshi Nishikawa, Tokai (JP); Shoji Morita, Nagoya (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/876,968

(22) PCT Filed: Jun. 26, 2012

(86) PCT No.: PCT/JP2012/004118
§ 371 (c)(1), (2), (4) Date: Mar. 29, 2013

(87) PCT Pub. No.: WO2014/002134
PCT Pub. Date: Jan. 3, 2014

(65) Prior Publication Data
US 2014/0158522 A1      Jun. 12, 2014

(51) Int. Cl.
*B01J 19/12*     (2006.01)
*C07C 249/04*    (2006.01)
*C07C 249/06*    (2006.01)

(52) U.S. Cl.
CPC ............ *C07C 249/06* (2013.01); *B01J 19/123* (2013.01); *B01J 19/127* (2013.01); *C07C 2101/14* (2013.01)

(58) Field of Classification Search
CPC .. C07C 249/06; C07C 2101/14; B01J 19/123; B01J 19/127; B01J 2219/00936; B01J 2219/00943
USPC ................................................... 204/157.83
See application file for complete search history.

(56) References Cited

U.S. PATENT DOCUMENTS 2,885,332 A * 5/1959 Mueller et al. ........... 204/157.83
2,885,333 A * 5/1959 Mueller et al. ........... 204/157.83
(Continued)

FOREIGN PATENT DOCUMENTS

CH       493935 A  *  7/1970
DE       1668720 B2 *  4/1973
(Continued)

OTHER PUBLICATIONS

English-language translation of Description of FR1535102A.*
(Continued)

*Primary Examiner* — Keith Hendricks
*Assistant Examiner* — Colleen M Raphael
(74) *Attorney, Agent, or Firm* — DLA Piper LLP (US)

(57) ABSTRACT

A method produces a cycloalkanone oxime by photonitrosation using light emitting diodes as the light source for the next generation that replaces an electric discharge lamp with, for example, mercury or sodium sealed therein. The method produces the cycloalkanone oxime by a photochemical reaction of a cycloalkane with a photo nitrosating agent in a liquid by light irradiation. The method uses a light source satisfying conditions that, in an emission energy distribution with respect to wavelength of the light source, a wavelength at which emission energy has a maximum value is in a range of 550 nm to 700 nm and a wavelength range outputting energy of or over 5% strength of the peak strength is equal to or less than 150 nm. An irradiation distance in the liquid is equal to or greater than 200 mm, and concentration of the photo nitrosating agent in the liquid is 0.1 mol % to 0.5 mol %.

6 Claims, 2 Drawing Sheets

(56) References Cited

U.S. PATENT DOCUMENTS

| | | | | |
|---|---|---|---|---|
| 2,985,572 A * | 5/1961 | Von Schickh et al. | ... | 204/157.84 |
| 3,047,481 A * | 7/1962 | Kahr | ... | 204/157.83 |
| 3,047,482 A * | 7/1962 | Taub et al. | ... | 204/157.83 |
| 3,048,634 A * | 8/1962 | Mueller et al. | ... | 204/157.83 |
| 3,062,812 A * | 11/1962 | Taylor | ... | 204/157.83 |
| 3,090,739 A * | 5/1963 | Ito | ... | 204/157.83 |
| 3,177,133 A * | 4/1965 | Metzger et al. | ... | 204/157.83 |
| 3,218,247 A * | 11/1965 | Torimitsu et al. | ... | 204/157.83 |
| RE25,937 E * | 12/1965 | Ito | ... | 204/157.83 |
| 3,239,508 A * | 3/1966 | Ito et al. | ... | 540/464 |
| 3,284,330 A * | 11/1966 | Ito et al. | ... | 204/157.83 |
| 3,309,298 A * | 3/1967 | Torimitsu et al. | ... | 204/157.84 |
| 3,312,612 A * | 4/1967 | Choo | ... | 204/157.83 |
| 3,320,143 A * | 5/1967 | Baumgartner et al. | ... | 204/157.83 |
| 3,344,187 A * | 9/1967 | Caprara et al. | ... | 204/157.83 |
| 3,393,139 A * | 7/1968 | Wakamatsu et al. | ... | 204/157.83 |
| 3,427,303 A * | 2/1969 | Kern et al. | ... | 540/482 |
| 3,479,264 A * | 11/1969 | Wakamatsu et al. | ... | 204/157.83 |
| 3,498,895 A * | 3/1970 | Streltsova | ... | 204/157.84 |
| 3,537,964 A * | 11/1970 | Eiga et al. | ... | 204/157.83 |
| 3,544,438 A * | 12/1970 | de Boer et al. | ... | 204/157.83 |
| 3,553,091 A * | 1/1971 | Nishikawa et al. | ... | 204/157.83 |
| 3,635,807 A * | 1/1972 | Guarino et al. | ... | 204/157.83 |
| 3,652,552 A * | 3/1972 | Garritsen et al. | ... | 204/157.69 |
| 3,681,217 A * | 8/1972 | Lucas et al. | ... | 204/157.83 |
| 3,681,218 A * | 8/1972 | Lucas et al. | ... | 204/157.83 |
| 3,717,561 A * | 2/1973 | Rigdon et al. | ... | 204/157.83 |
| 3,734,845 A * | 5/1973 | Bravi et al. | ... | 204/157.83 |
| 3,853,729 A * | 12/1974 | Lucas | ... | 204/157.83 |
| 5,054,018 A * | 10/1991 | Tremblay | ... | 398/42 |
| 5,719,316 A * | 2/1998 | Ollivier | ... | 204/157.83 |
| 6,197,999 B1 * | 3/2001 | Ollivier et al. | ... | 204/157.83 |
| 2007/0035813 A1 * | 2/2007 | Roth et al. | ... | 359/350 |
| 2009/0207604 A1 * | 8/2009 | Robotham | ... | 362/230 |
| 2011/0137027 A1 | 6/2011 | Aubert | | |

FOREIGN PATENT DOCUMENTS

| | | | |
|---|---|---|---|
| EP | 0 989 118 | | 3/2000 |
| EP | 1 995 834 | | 11/2008 |
| FR | 1334932 A | * | 8/1963 |
| FR | 1535102 A | * | 8/1968 |
| GB | 888725 A | * | 2/1962 |
| GB | 977812 A | * | 2/1962 |
| GB | 1017242 A | * | 1/1966 |
| GB | 1019544 A | * | 2/1966 |
| GB | 1066114 A | * | 4/1967 |
| GB | 1136116 A | * | 12/1968 |
| GB | 1136747 A | * | 12/1968 |
| GB | 1183109 A | * | 3/1970 |
| GB | 1188216 A | * | 4/1970 |
| GB | 1345481 A | * | 1/1974 |
| GB | 1354183 A | * | 6/1974 |
| GB | 1345481 A | * | 7/1977 |
| JP | 45-019695 B | | 7/1970 |
| JP | 2001-2636 | | 1/2001 |
| JP | 2008-86993 | | 4/2008 |
| JP | 2010-006775 | | 1/2010 |
| JP | 2010-006776 | | 1/2010 |
| JP | 2011-521004 | | 7/2011 |
| JP | 2012-149055 | | 8/2012 |
| SU | 228032 A | * | 3/1969 |
| WO | 2004/068182 | | 8/2004 |
| WO | 2007/142946 | | 12/2007 |

OTHER PUBLICATIONS

Naylor et al, "Synthesis of cyclohexanone oxime by photoreaction of nitrosyl chloride with cyclohexane," J. Org. Chem. 1953, 18(1), pp. 115-120.*

US Department of Energy, "Energy Efficiency of LEDs," PNNL-SA-94206, Mar. 2013, available online at http://apps1.eere.energy.gov/buildings/publications/pdfs/ssl/led_energy_efficiency.pdf.*

"Kagaku Jiten," *Tokyo Kagaku Dojin*, pp. 457-458 and 1 page with partial English translation.

*Journal of the Japan Petroleum Institute*, 1974, vol. 17, No. 10, pp. 72-77 and 1 page with partial English translation.

English translation of Arkema France's Opposition dated Jul. 8, 2015 to EP Patent No. 2695879/12832790.5.

"Beer-Lambert law," Wikipedia, https://en.wikipedia.org/wiki/Beer%E2%80%93Lambert_law.pdf.

Luxeon Rebel, Philips, Technical Datasheet DS56, 2008.

Luxeon III Emitter, Philips, Technical Datasheet DS45, 2006.

H. Miyama, et al., "Quantim Yield of Photonitrosation of Cyclohexane in Homogeneous System," *The Journal of Physical Chemistry*, Jun. 30, 1969, vol. 73, No. 12, pp. 4345-4347.

PhlatLight PT54 Projection Chipset product data sheet, Luminus Devices, Inc., 2007, http://www.mouser.comicatalog/specsheets/pt54phlatlight.pdf.

"Kagaku Kogaku," *The Society of Chemical Engineers*, vol. 60, No. 8, pp. 580-582 w/ English abstract.

* cited by examiner

METHOD OF PRODUCING CYCLOALKANONE OXIME

TECHNICAL FIELD

This disclosure relates to a method of producing a cycloalkanone oxime by photonitrosation.

BACKGROUND

A photoreaction means the general chemical reaction that causes molecules (i.e., radical reactant) to absorb energy by light irradiation, to be excited to the state of the higher energy level (i.e., excited state) and thereby to induce the reaction. The photoreaction is also called a photochemical reaction. According to "Kagaku Jiten" p 457-458, Tokyo Kagaku Dojin, photoreactions include oxidation-reduction reactions by light and substitution and addition reactions by light. As is known, a photoreaction is applicable to not only photographic industries, photocopying technology, induction of photovoltaic power, but syntheses of organic compounds. Photochemical smog is also the unintentional photochemical reaction.

As described in JP 2010-6775A or *Journal of the Japan Petroleum Institute*, Vol. 17, No. 10 (1974) p 72-76, there is a known technique of synthesizing cyclohexanone oxime by a photochemical reaction. It is also known that the wavelength of 400 to 760 nm is desirable as the effective wavelength for the reactions of a cycloalkanone oxime. Examples of the light emitter having the energy output characteristics specialized in such specific wavelength range include light sources such as light emitting diodes, lasers and organic electroluminescence (organic EL).

Light emitting diodes have the advantage of directly converting electrical energy into light with a semiconductor. The light emitting diodes attract attention because of less heat generation, efficient use of energy and long life. With recent development of LEDs of high efficiency and high output, LEDs can replace incandescent lamps and fluorescent lamps in general lighting purposes. As for industrial purposes, LEDs are expected to reach the practical level in several years.

In such an environment, the method of producing a cycloalkanone oxime proposed in JP 2010-6775A has the following characteristics: (i) It is preferable that in the emission energy distribution with respect to the wavelength of the light source, the emission energy in the wavelength range of less than the wavelength of 400 nm is equal to or less than 5% of the maximum value of emission energy and the emission energy in the wavelength range of greater than the wavelength of 760 nm is equal to or less than 5% of the maximum value of emission energy. (ii) The light emitting diodes have an energy conversion efficiency equal to or greater than 3%. (iii) A plurality of light emitting diodes arrayed in a plane along the side face of a photochemical reactor containing a photoreaction liquid are used to irradiate the photochemical liquid with light via a permeable photochemical reactor.

According to the technique described in JP 2010-6776A, cyclohexanone oxime is synthesized under the following conditions. Light emitting diodes are used as the light source. In the emission energy distribution with respect to the wavelength of the light source, the wavelength at which emission energy has a maximum value is 400 nm to 760 nm. A cooling jacket is provided on the rear face of the light source to continuously introduce a coolant to the cooling jacket and forcibly and indirectly cool down the light source. In the emission energy distribution with respect to the wavelength of the light source, the wavelength at which emission energy has a maximum value is 430 nm to 650 nm. The integrated value of emission energy at the wavelengths of 400 nm to 760 nm relative to the emission energy in the wavelength range of 300 nm to 830 nm is equal to or greater than 95%. JP 2010-6776A additionally includes descriptions on the temperature of the coolant introduced into the cooling jacket, the method of arranging the light emitting diodes, and the minimum distance of irradiation between the light emitting diodes and the side face of the photochemical reactor. JP 2011-521004A describes photonitrosation of a cycloalkanone oxime conducted in a very small space with a microreactor using light emitting diodes.

The amount of the cycloalkanone oxime produced per unit electric power by the method described in any of the publications above is, however, not sufficiently high compared to the industrially practical level. There is thus a requirement for further improvement of the utilization efficiency of energy.

It could therefore be helpful to provide a production method that produces a cycloalkanone oxime at a high yield by photonitrosation using a light source having a narrow wavelength distribution and thereby enables power saving and resource saving in production of the cycloalkanone oxime.

SUMMARY

We found that controlling the contact time of light with the reaction field or the irradiation distance and controlling the concentration of a nitrosating agent excited by light in the reaction field enables a significant increase in the amount of cycloalkanone oxime produced.

We thus provide:
(1) A method of producing a cycloalkanone oxime by a photochemical reaction of a cycloalkane with a photo nitrosating agent in a liquid by light irradiation.
    The method uses a light source configured to emit light satisfying conditions that, in an emission energy distribution with respect to wavelength of light, a wavelength at which emission energy has a maximum value is in a range of 550 nm to 700 nm and a continuous wavelength range including the wavelength at which the emission energy has the maximum value and outputting energy of or over 5% strength of the maximum value is equal to or less than 150 nm.
    An irradiation distance in the liquid is equal to or greater than 200 mm, and concentration of the photo nitrosating agent in the liquid is 0.1 mol % to 0.5 mol %.
(2) The method of producing the cycloalkanone oxime described in (1), wherein the light source is a light emitting diode.
(3) The method of producing the cycloalkanone oxime described in either one of (1) and (2), wherein the light source has an energy conversion efficiency equal to or greater than 10%.
    The light source may, however, have the energy conversion efficiency of less than 10%.
(4) The method of producing the cycloalkanone oxime described in any one of (1) to (3), wherein the light source has an energy conversion efficiency equal to or greater than 20%.
(5) The method of producing the cycloalkanone oxime described in any one of (1) to (4), wherein the wavelength at which the emission energy has the maximum value is in a range of 600 nm to 650 nm.
    The wavelength at which the emission energy has the maximum value may, however, be less than 600 nm or may be greater than 650 nm.

(6) The method of producing the cycloalkanone oxime described in any one of (1) to (5), wherein the cycloalkane is cyclohexane, and the cycloalkanone oxime is cyclohexanone oxime.

(7) The method of producing the cycloalkanone oxime described in any one of (1) to (6), wherein the photo nitrosating agent is nitrosyl chloride.

We thereby significantly improve the yield of a cycloalkanone oxime as the target product. Additionally, we enable reduction of impurity generation, as well as reduction of power consumption, thus allowing power saving and reduction of the amount of a cycloalkane used as the material.

REFERENCE SIGNS LIST

1 Light Emitting Diode
2 Photochemical Reactor
3 Heat Sink
4 Cycloalkane Supply Line
5 Photo Nitrosating Agent Supply Line
6 Cooler
7 Reaction Cooling Water Supply Line
8 Reaction Cooling Water Discharge Line
9 Unreacted Gas Line
10 Reaction Product Line
11 Photochemical Reactor (Variable Irradiation Distance)
12 Circuit Base for Irradiation of Light Emitting Diodes
13 Light Emitting Diode-Exposure Electrode Substrate
14 Light Emitting Diode (Light Emitting Element)
15 Reactor Input Material Circulation Line
16 Reaction Liquid Circulation Line
17 Reactor Input Material Circulation Line Pump
18 Reaction Liquid Circulation Line Pump
21 Nitrosyl Chloride Injection Line
22 Nitrosyl Chloride-Unreacted Gas Extraction Line
23 Oily Product Extraction Line
24 Separator
25 Material Supply Line

DETAILED DESCRIPTION

The light source in one example is a light emitting diode. The light emitting diode is a semiconductor element that emits light by utilizing electroluminescence (EL) effect. The light emitting diode emits light under application of a voltage in the forward direction. The light emitting diode is also referred to as LED. The following describes one example using light emitting diodes as the light source, but any other light source that satisfies the condition (1) described above such as laser or organic electroluminescence (organic EL), may be adopted for the light source.

Figure 1:
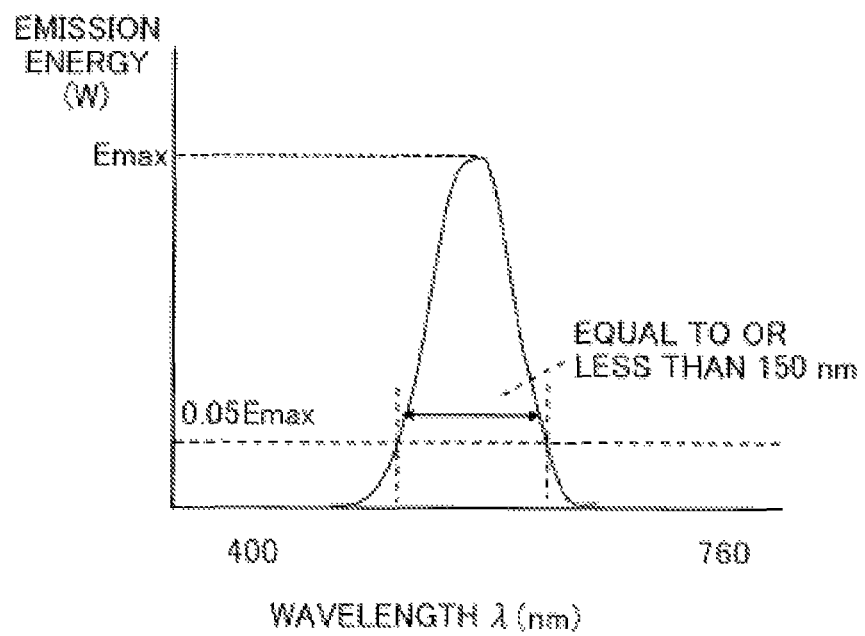
FIG. 1 is a graph showing one example of the emission energy distribution of a light emitting diode used in one example having the maximum value of emission energy at the wavelength about 615 nm.

A preferable example of emission energy distribution with respect to the wavelength of a light emitting diode used in one example is described with reference to FIG. 1. The "emission energy distribution" is a spectral distribution as shown in FIG. 1 with the wavelength as the abscissa axis and the emission energy as the ordinate axis. FIG. 1 is a graph showing one example of emission energy distribution of a light emitting diode used in one example having the maximum value of emission energy at the wavelength about 615 nm. In FIG. 1, the unit of the ordinate axis is watt (W) and the unit of the abscissa axis is nanometer (nm).

The "maximum value of emission energy" represents the highest value of emission energy in the emission energy distribution with respect to the wavelength measured in every 5 nm wavelength ranges. Hereinafter, the maximum value of emission energy is also called "peak strength" and is expressed as Emax. The wavelength at which the emission energy has the maximum value is called "peak wavelength". The "peak wavelength" represents the median value in a wavelength range having the "peak strength" in the emission energy distribution measured in every 5 nm wavelength ranges.

This example uses a light emitting diode that emits light satisfying the conditions that, in the emission energy distribution with respect to the wavelength, the peak wavelength is 550 nm to 700 nm and the width of the continuous wavelength range including the peak wavelength and outputting the energy of or over 5% strength of the peak strength Emax is equal to or less than 150 nm (FIG. 1). The peak wavelength is more preferably 600 nm to 650 nm and is further more preferably 610 nm to 620 nm. In the emission energy distribution, the width of the continuous wavelength range including the peak wavelength and outputting the energy of or over 5% strength of the peak strength Emax is preferably equal to or less than 100 nm and is more preferably equal to or less than 50 nm.

The "width of the continuous wavelength range outputting the energy of or over 5% strength of the peak strength Emax" represents the interval between the median values of wavelength ranges on both ends of one or more continuous wavelength ranges that have energy of or over 5% strength of the peak strength Emax in the emission energy distribution with respect to the wavelength measured in every 5 nm wavelength ranges. In the emission energy distribution with respect to the wavelength measured in every 5 nm wavelength ranges, however, when there is only one "continuous wavelength range including the peak wavelength and outputting the energy of or over 5% strength of the peak strength Emax", the "width of the continuous wavelength range outputting the energy of or over 5% strength of the peak strength Emax" is assumed to be 5 nm.

The reason why such emission energy distribution as described above is preferable is theoretically attributable to the following. More specifically, the photon energy required for radical dissociation of a nitrosating agent, for example, nitrosyl chloride, is obtained by the light having a wavelength equal to or less than 760 nm. In the emission energy distribution, substantially all photons have the wavelength equal to or less than 760 nm on conditions that (i) the wavelength range (width) including the peak wavelength having Emax and outputting the energy having the strength of or over 5% of Emax is equal to or less than 50 to 100 nm and (ii) the peak wavelength is equal to or less than 700 nm. As a result, substantially all the energy is in the wavelength range that is effective for radical dissociation. When the irradiated light has an excessively small wavelength, however, there is a high possibility of causing a side reaction. This example accordingly uses the light emitting diode satisfying the condition that the peak wavelength at which the emission energy has the maximum value is equal to or greater than 550 nm.

According to this example, the emission energy distribution may be measured by the method described later. The emission energy distribution in the application using a plurality of light emitting diodes is obtained by measuring the emission energy distributions of the individual light emitting diodes used and subsequently summing up the measured emission energy distributions of all the light emitting diodes used. In this case, the wavelength at which the emission energy has the maximum value (Emax) in the resulting emission energy distribution thus obtained should be 550 nm to 700 nm. When the plurality of light emitting diodes are light emitting diodes from one identical lot and apparently have equal quality, the simplified method may be adopted to measure the emission energy distribution of any arbitrary light emitting diode and determine whether the shape of the measured distribution satisfies the above conditions. In the application using multiple different groups of light emitting diodes, the simplified method may be adopted to measure the emission energy distribution of a light emitting diode sample selected from each group of light emitting diodes having equal quality and sum up the respective measured emission energy distributions weighted corresponding to the number of light emitting diodes belonging to each group to obtain the overall emission energy distribution.

The wavelength range in the emission energy distribution includes the ranges of ultraviolet light, visible light and near-infrared light. According to this example, it may be determined whether the emission energy distribution satisfies the above conditions, based on the energy spectrum of 300 to 830 nm that is detectable with at least a standard emission spectral measurement device. This is because the generally manufactured light emitting diode for generation of visible light typically outputs emission energy of or over 99% in the range of 300 nm to 830 nm.

The lighting properties of the light emitting diode are affected by the value of drive current and the temperature. The measurement of the emission energy distribution is accordingly performed under the same conditions of drive current and temperature as those adopted during light irradiation for the photochemical reaction. In other words, the measurement of the emission energy distribution is performed under the condition that the drive current applied to the light emitting diode as the subject of measurement of the emission energy distribution is substantially equal to the average value of drive current applied to each light emitting diode during light irradiation for the photochemical reaction. The amount of electric current applied for the photochemical reaction is preferably 0.1% to 100% of the rated current value of the light emitting diode used. The measurement is also performed under the condition that the surface temperature on the rear face of the light emitting diode is substantially equal to the average temperature of the light emitting diode during light irradiation by the light emitting diode for the photochemical reaction. When the rear face of the light emitting diode is equipped with, for example, a radiator plate, a circuit board with radiator plate or a heat sink, the measurement is performed under the temperature condition that the surface temperature of such element is substantially equal to the average temperature during the photochemical reaction. When the light emitting diode is mounted on, for example, a substrate, the measurement is performed under the temperature condition that the surface temperature of, for example, the substrate is substantially equal to the average temperature during the photochemical reaction.

The material of, for example, the radiator plate, the circuit board with radiator plate or the heat sink provided on the rear face of the light emitting diode may be aluminum or copper having good thermal conductivity. During the measurement, for example, a radiator plate, a circuit board with radiator plate or a heat sink may be provided on the light emitting diode to release heat from the light emitting diode or in some cases to cool down the light emitting diode to regulate the temperature substantially equal to the temperature during the photochemical reaction. The light emitting diode generates heat during operation to increase the temperature. The measurement time should be 10 to 300 ms to prevent a temperature rise over 1° C. The temperature during light irradiation for the photochemical reaction should be the average value of the surface temperature of, for example, the radiator plate, the circuit board with radiator plate or the heat sink of the light emitting diode.

The emission energy distribution is obtained by measurement of the output in every 5 nm wavelength ranges. When the more accurate measurement is required, the emission energy distribution is obtained preferably by measurement of the output in every 0.5 to 1 nm wavelength ranges. The center value in the wavelength band of the measured output should be used for evaluation of the wavelengths such as the peak wavelength and the wavelength range (width) outputting the energy having the strength of or over 5% of Emax. When the measurement is performed prior to the photochemical reaction, the measurement should be performed under the conditions of temperature and drive current expected for the photochemical reaction. According to this example, it is preferable to set the temperature at −20° C. to 50° C. as long as the temperature range does not interfere with the reaction in the liquid. The light emitting diode itself is not exposed to the liquid. The temperature range should thus be the range that does not solidify the liquid on the surface irradiated with the light from the light emitting diode. The more preferable temperature is −10° C. to 40° C. This temperature range does not cause evaporation of cyclohexane, one example of a cycloalkane used for production of a cycloalkanone oxime. The lower temperature, however, causes the higher light emitting efficiency, because of the characteristics of the light emitting diode.

In the light emitting diode used according to this example, the energy conversion efficiency η, i.e., the integrated value of emission energy (effective energy) in the wavelength range of 400 to 760 nm with respect to the input electric power per each light emitting diode, is preferably equal to or greater than 10% or more preferably equal to or greater than 20%. There is no specific limitation on the upper limit of the energy conversion efficiency η. Based on the theoretical upper limit of the external quantum efficiency (the ratio of the number of photons taken outside to the number of input electrons), the upper limit of the energy conversion efficiency is 75%, for example, at the wavelength about 400 nm in the above wavelength range of 400 to 760 nm. The energy conversion efficiency of 75% has the sufficient advantageous effects, and the energy conversion efficiency of even 60% or less still has the sufficient advantageous effects by reducing the amount of heat generation compared with an electric discharge lamp. The LED (Luxeon LXML-PL01-0030 manufactured by Philips Lumileds Lighting Company) used in PTL3 has the energy conversion efficiency as low as 7% and does not have the efficient reaction result relative to the input electric power.

According to this example, an integrating sphere (PMA-12 manufactured by Hamamatsu Photonics K.K.) is used as the device to measure the emission energy in the wavelength distribution. The integrating sphere enables measurement of the absolute value of emission energy at each wavelength.

The integrating sphere includes a micro-spectrometer, a high-sensitive multi-channel photo detection element, a current-voltage regulator and a controller. The procedure first detects the photo energy in each wavelength range with the photo detection element while fixing the electric current applied to the light emitting diode to a certain value. The procedure then successively shifts the wavelength range for detection to measure the energy distribution in each wavelength range. On completion of the wavelength shift and the detection with respect to the certain current value, the controller changes the setting to a next current value and repeats the wavelength shift and the detection as described above. The integrating sphere can automatically measure the electric current-wavelength distribution by this procedure. The width of varying the current value (current span), the wavelength range and the width of varying the wavelength (wavelength span) may be changed freely. The measurement of this examination adopts the current span of 100 mA and the wavelength span of 1 nm. These spans are, however, not restrictive, but may be changed according to the purpose of the examination.

According to this example, the integrating sphere has the inner diameter of or over 3 inches (7.6 cm). In the case of difficulty in measurement, however, the integrating sphere having the inner diameter of or over 10 inches (25.4 cm) is used. The measurement width at each wavelength is preferably equal to or less than 5 nm and is more preferably in the range of 0.5 to 1 nm.

The "selection rate" according to this example shows the ratio of the produced amount of a cycloalkanone oxime as the target product to the conversion amount of a cycloalkane containing impurity. The "selection rate" is calculated as the value of the molar amount of the produced cycloalkanone oxime as the numerator to the total molar amount of the produced cycloalkanone oxime and the produced impurity as the denominator. The selection rate closer to 100% proves that the cycloalkane is used effectively and the target product is obtained efficiently. The analytical values by gas chromatography are used for such measurement.

Figure 2:
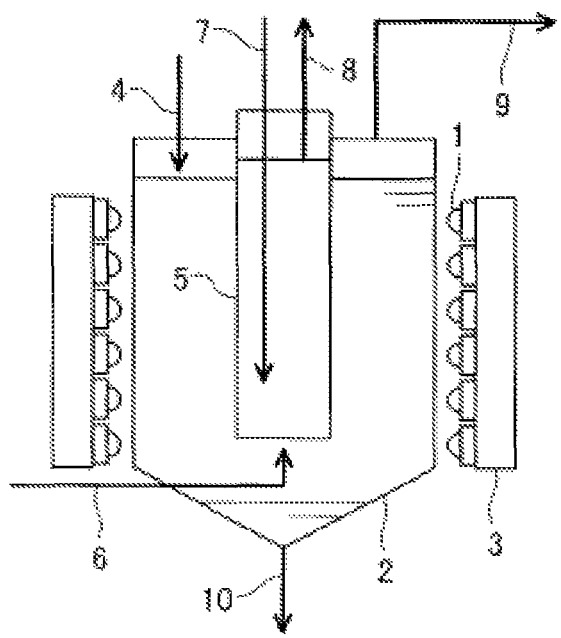
FIG. 2 is a conceptual cross sectional diagram showing one example of a photochemical reactor using light emitting diodes.

The following describes one example of the photochemical reaction using light emitting diodes with reference to FIG. 2. FIG. 2 is a conceptual cross sectional diagram illustrating one example of a photochemical reactor using light emitting diodes.

Light emitting diodes 1 used as the light source in this example may be any of general bombshell type, surface mount type or chip type. The light emitting diodes 1 allowing heat release over the wide area of the rear face are, however, preferable to reduce the temperature increase of a photoreactive liquid in a photochemical reactor 2 located in the light irradiating direction of the light emitting diodes 1.

Any method may be adopted for light irradiation from the light source as long as a photoreactive liquid of a cycloalkane and a photo nitrosating agent or a photoreactive liquid containing their reaction products is effectively irradiated with the light. The method of light irradiation may be, for example, an external irradiation type of irradiating the photoreactive liquid with light from outside of a photochemical reactor 2 as shown in FIG. 2 or an internal irradiation type of directly or indirectly soaking a light source in the photoreactive liquid and irradiating the photoreactive liquid with light from inside of the photochemical reactor 2. The conventional lamps such as electric discharge lamps and fluorescent lamps are the light sources mainly in the spherical shape or in the bar-like shape. To ensure the effective use of the light from such light source, the internal irradiation is predominant as the conventional light irradiation method. The internal irradiation has additional advantage that freely changes the distance of irradiating the reaction liquid with the same light emitter.

The reactor having an array of a large number of small point light sources such as light emitting diodes may, however, be in any shape. The most advantageous shape for the reaction rate and the easiness of construction may be selected as the shape of the reactor. The light emitting diodes 1 are bonded to heat sinks 3 by, for example, a heat conductive adhesive and release heat outside of the light emitting diodes 1. A cycloalkane is supplied through a cycloalkane supply line 4 to the photochemical reactor 2 and is discharged with a product of a higher specific gravity through a reaction product line 10. The photo nitrosating agent in this example is a gaseous agent. The photo nitrosating agent is supplied through a photo nitrosating agent supply line 5 to the photochemical reactor 2 and discharged a non-reactive gas line 9 after absorption of the nitrosating agent into the reaction liquid. The photo nitrosating agent is the gaseous agent according to this example, but may be a liquid agent such as trichloronitrosomethane. The temperature of the reaction tank is controlled by making the flow of cooling water through a cooling water supply line 7 to a cooler 6 and discharging the cooling water after cooling through a cooling water discharge line 8. To keep the temperature of the reaction tank at or over 10° C., it is preferable to use water of or below 10° C. as the coolant. Using the cooling water having the temperature difference of at least a predetermined value from the target temperature of the reaction tank enables the temperature of the reaction tank to be effectively controlled by regulating the flow rate of the cooling water.

The "irradiation distance" in the liquid represents the distance of the light that passes through the wall surface of the transparent material of the reactor to radiate inwardly and reaches the obstacle or the wall surface. In the illustrated example of FIG. 2, the irradiation distance is the distance from the wall surface of the glass reaction tank to the wall surface of the liquid-cooling part located in the center of the reaction tank when the light is emitted toward the center of the liquid-cooling part in the vertical cylindrical shape. For example, the reaction tank used in the experiment of Table 1 described in JP 2010-6775A is formed in the same shape as that of FIG. 2, wherein the diameter of the reaction tank is 14 cm and the diameter of the internal liquid-cooling part is 5 cm. The irradiation distance is accordingly 4.5 cm (45 mm). The internal irradiation type having the light emitter located in the center of the reactor of FIG. 2 to radiate light outwardly has the substantially similar irradiation distance. The longer irradiation distance is generally thought to be desirable for light absorption, and it is generally thought that the irradiation distance is preferably equal to or greater than the distance required for absorption of all the irradiated light. In the actual state, however, the light absorption proceeds according to Equation (1) given below by the Lambert-Beer's law on light absorption. The excessive irradiation distance is accordingly not effective. The higher light absorption rate is desirable, and the light absorption rate equal to or higher than 50% is preferable from the practical point of view. In Equation (1) given below, the concentration c of the nitrosating agent may be expressed by the percent by weight or the percent by mole by setting an adequate value to a coefficient α:

$$\text{Light Absorption Rate} = 1 - \exp(-\alpha \cdot C \cdot L) \quad (1)$$

where α represents the coefficient, L represents the irradiation distance and c represents the concentration of the nitrosating agent.

The higher concentration of the photo nitrosating agent is generally thought to be desirable for the greater absorption of the irradiated light. The high concentration of the photo nitrosating agent, however, causes the high possibility of side reaction, which may increase the amount of impurity and decrease the selection rate described later. The excessively low concentration of the photo nitrosating agent, on the other hand, causes insufficient light consumption due to the poor light absorption, which may decrease the produced amount of a cycloalkanone oxime per unit energy. Based on these phenomena, it is preferable to increase the concentration of the photo nitrosating agent to such an extent that does not increase production of the impurity and thereby enhance the light absorption rate.

In the wavelength range specified according to this example, the following values are preferable as the irradiation distance and the concentration of the photo nitrosating agent in the liquid. The irradiation distance is preferably equal to or greater than 200 mm and is more preferably in the range of 200 mm to 600 mm. The concentration of the photo nitrosating agent in the liquid is preferably in the range of 0.1 percent by mole to 0.5 percent by mole and is more preferably in the range of 0.2 percent by mole to 0.4 percent by mole. Setting the irradiation distance and the concentration of the photo nitrosating agent in the liquid to such ranges enables the irradiated light to be absorbed by a radical reaction initiator and expects the relatively high selection rate. The calculation by the Lambert-Beer's law gives the light absorption rate of at least 50% under the conditions of the irradiation distance and the concentration of the photo nitrosating agent of the above ranges and gives the light absorption rate of at least 80% under the preferable conditions.

For the purpose of further controlling the irradiation distance, for example, a reaction device including a photochemical reactor of the variable volume (variable volume reactor) 11 may be provided to change the length of the photochemical reactor 11 in the light irradiation direction and determine the desirable irradiation distance. Such a reaction device may be used for industrial production, although the features of the example are not at all restricted by the shape of this reaction device.

Figure 3:
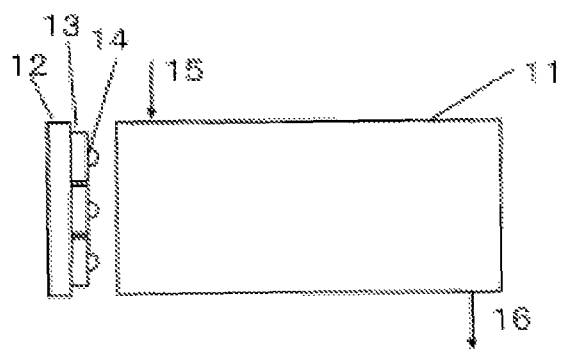
FIG. 3 illustrates one example of an apparatus used for a photoreaction experiment in which the irradiation distance is changed.

FIG. 3 is a conceptual side view illustrating one example of a reaction device used for a photoreaction experiment with changing the irradiation distance described later. A plurality of light emitting diode-exposure electrode substrates 13 having light emitting diodes 14 mounted thereon and electrodes for circuit connection exposed outside of the light emitter are placed on the same side relative to the photochemical reactor 11. This structure enables the irradiated light to be introduced into the photochemical reactor 11. The light emitting diodes (light emitting elements) 14 are ultra-small light sources. Light emitters or modules with arrays of a plurality of light emitting diodes may be combined in any form that allows construction of the circuit. This enables light irradiation in various shapes that are not readily achievable by the electric discharge lamp and enables objects in various shapes such as plane and curved surface to be irradiated with light. The light-emitting diodes have high directional characteristics, so that the array of the plurality of light emitting diodes on the light emitter (module) enables uniform light emission of the light emitter (module).

The material for the side face of the transparent photochemical reactor 11 may be any material that has the good transmission property of the light emitted from the light emitting diodes used, for example, glass, crystal or transparent resin such as acrylic resin. The part that is not subjected to light transmission is preferably covered with, for example, an aluminum foil to prevent dissipation of the irradiated light. When the liquid placed inside the reactor is corrosive, the reactor is preferably made of glass. In the application that produces the part that is not subjected to light transmission from a different material, titanium or tantalum may also be used as the material.

There is no specific limitation on the temperature for emission of the light emitting diodes (light emitting elements) 14. Emission of the light emitting diodes (light emitting elements) 14 is affected by the ambient temperature such as outside air temperature and the temperatures of the joints of the light emitting diodes, the substrate and the radiator plate. In general, the higher temperature causes the lower emission energy per unit electric power. It is accordingly preferable to reduce a temperature rise of the light emitting diodes. As long as the photonitrosation is enabled, the lower temperature of the light emitting diodes is preferable. One available method of reducing a temperature rise during emission of the light emitting diodes 14 may be the air-cooling method when the ambient temperature is substantially constant and the air-cooling method can sufficiently prevent heat generation of the light emitting diodes and reduce a temperature rise during emission of the light emitting diodes. For example, a heat sink made of a metal such as aluminum or copper may be provided on the rear surface of light emitting diode-exposure electrode substrates 13 or a circuit base 12 for irradiation of light emitting diodes. To enhance the contact area with the outside air, the heat sink may have, for example, fins to release heat. The cooling method using a coolant may be adopted for the same purpose. From the practical point of view, the target temperature of the temperature control is preferably equal to or higher than 0° C. Any cooling substance, for example, water, an organic cooling liquid, an inorganic cooling liquid, the air or nitrogen may be used as the coolant. When cyclohexane is used as the material, it is preferable to use chilled water of 4 to 10° C. according to the relationship to the melting point of cyclohexane.

There is no specific limitation on the number of carbons included in the cycloalkane according to the example. Preferable examples of the cycloalkane include cyclopropane, cyclobutane, cyclopentane, cyclohexane, cycloheptane, cyclooctane, cyclononane, cyclodecane, cycloundecane and cyclododecane. Especially preferable are cyclohexane as the material of caprolactam and cyclododecane as the material of lauryl lactam.

The cycloalkane may be supplied, for example, through a reactor input material circulation line 15 to the photochemical reactor 11 (FIG. 3). The cycloalkane containing a gaseous photo nitrosating agent injected in advance and adjusted to a predetermined concentration is used as the supply liquid. This enables supplement of the photo nitrosating agent consumed in the reactor. Alternatively the reaction may be conducted, with continuously injecting the photo nitrosating agent into the supply liquid. In the latter case, the preferable procedure may control the injection amount of the photo nitrosating agent with monitoring the concentration of the photo nitrosating agent in the reaction liquid.

Nitrosyl chloride or trichloronitrosomethane may be used as the photo nitrosating agent. Another available example may be a gas that reacts and produces the photo nitrosating agent. For example, any of a mixed gas of nitrosyl chloride and hydrogen chloride, a mixed gas of nitrogen monoxide and chlorine, a mixed gas of nitrogen monoxide, chlorine and hydrogen chloride and a mixed gas of dinitrogen trioxide gas and chlorine reacts in the photoreaction system and acts as nitrosyl chloride. The supply form of the nitrosating agent is accordingly not limited. Trichloronitrosomethane obtained by photoreaction of nitrosyl chloride and chloroform may also be used as the nitrosating agent. The concentration of the photo nitrosating agent may be measured for sampled liquid by iodine color change and titration with sodium thiosulfate as described later or may be determined by the simplified method using light transmission rate. The concentration of the photo nitrosating agent may be adjusted by regulating the amount of nitrosyl chloride in the reaction liquid.

The photochemical reaction of the cycloalkane and the photo nitrosating agent by light irradiation from the light emitting diodes yields a cycloalkanone oxime corresponding to the number of carbons included in the cycloalkane.

The photochemical reaction in the presence of hydrogen chloride gives the cycloalkanone oxime in the form of a hydrochloride of cycloalkanone oxime. The cycloalkanone oxime may be kept in the hydrochloride form. For example, photonitrosation of cyclohexane by nitrosyl chloride gives cyclohexanone oxime. The resulting cyclohexanone oxime obtained by the reaction sediments in the tank of the photochemical reactor 11 to be accumulated as the oily product. This oily product is extracted via a reaction liquid circulation line 16 (FIG. 3). The unreacted liquid is discharged with the oily product via an unreacted cyclohexane+cyclohexanone oxime circulation line 16 and is separated from the oily product outside of the system by the specific gravity difference. In many cases, the unreacted substance is re-supplied as the material to the photoreaction tank.

Figure 4:
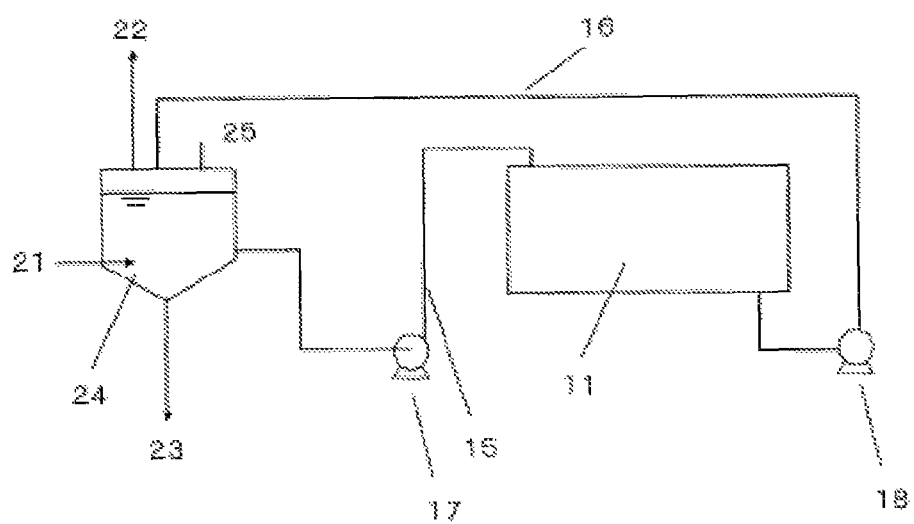
FIG. 4 illustrates one example of peripheral devices of the apparatus used for the photoreaction experiment in which the irradiation distance is changed.

FIG. 4 illustrates one example of peripheral devices of the apparatus of FIG. 3 used for the photoreaction experiment. Unreacted cyclohexane as the unreacted substance and cyclohexanone oxime as the oily product are introduced from the photochemical reactor 11 through the reaction liquid circulation line 16 to a separator 24 and are discharged by using a reaction liquid circulation line pump 18. Cyclohexane is separated from the oily product in the separator 24 by the specific gravity difference and is supplied back through the reactor input material circulation line 15 to the photochemical reactor 11 by using a reactor input material circulation line pump 17. In the separator 24, nitrosyl chloride is injected through a nitrosyl chloride injection line 21 and is absorbed into the cyclohexane. The unreacted gas is discharged through a nitrosyl chloride-unreacted gas discharge line 22. Cyclohexane oxime as the product is extracted through an oily product extraction line 23. An amount of cyclohexane corresponding to its decrease by extraction of the product may be supplied through a material supply line 25.

According to another example, the photochemical reaction may be conducted in an apparatus including a cylindrical reactor and a light emitter assembly (i.e., light emitter module) with a large number of light emitting diodes bonded outside of one single cylinder located in the reactor. In this case, the irradiation distance may be adjusted by regulating the diameter of the outer cylinder of the reactor. In another example, the irradiation distance may be adjusted by placing a baffle or a cooling plate in the irradiation direction to appropriately interfere with light irradiation. In the application using a plurality of light emitter modules for the reaction, the irradiation distance may be adjusted by regulating the distance between the light emitter modules, in addition to the outer cylinder, the baffle or the cooling plate, to an optimum value. Although there are technically clearances between adjacent light emitter modules, but the effect of light leaking through these clearances is only limited. There is no specific limitation on the arrangement of a plurality of light emitter modules in the horizontal plane. The triangular arrangement of placing the respective light emitter modules at the apexes of an equilateral triangle equalizes the distances between the respective light emitters and enables a greater number of light emitters to be placed in the limited area.

EXAMPLES

Our methods are described below more specifically with reference to examples.

The following specifies the conditions of the fundamental procedure of producing a cycloalkanone oxime according to examples and comparative examples. The cycloalkanone oxime is produced by changing part of these conditions to conditions specified in the respective examples and comparative examples.

A photochemical reaction apparatus similar to that shown in FIGS. 3 and 4 was used for the photoreaction experiment. Four "Pyrex (registered trademark)" glass cylinders commonly having the inner bore of 10 cm and differently having the lengths of 4.5 cm, 9 cm, 22.5 cm and 45 cm were used as the cylindrical photochemical reactor 11. Photoreaction tanks were successively replaced according to the irradiation distances set as the experimental condition, and data at the respective irradiation distances were measured. The light emitting diode-exposure electrode substrates 13, the circuit base 12 for irradiation of light emitting diodes and the light emitting diodes (light emitting elements) 14 working as the light source were provided as a commercially available integral product. As the light emitting diodes 14 used were light emitting diodes having the energy peak at the wavelength of 615 nm (light emitting diodes Red Orange LXML-PH01-0050 with the energy conversion efficiency of 20% manufactured by Philips Lumileds Lighting Company or light emitting diodes Red Orange XPERD0-1-0000-00701 with the energy conversion efficiency of 35% manufactured by Cree, Inc.) or light emitting diodes having the energy peak at the wavelength of 443 nm (light emitting diodes Cool White LXML-PW01-0040 with the energy conversion efficiency of 20% manufactured by Philips Lumileds Lighting Company) mounted on an aluminum circular substrate (TR-RE90φ75 manufactured by EFFECT Corporation) as the circuit base 12 for irradiation of light emitting diodes. All the light emitting diode-exposure electrode substrates 13 and the light emitting diodes 14 used were the products from the same lot. A light emitter module was structured by arranging ninety light-emitting diode-exposure electrode substrates 13 respectively having light emitting diodes 14 in a rectangular shape on the circular plate of 7.5 cmφ. An aluminum heat sink for cooling was attached to the light emitter module on the opposite side to the side with the light emitting diode-exposure electrode substrates 13. The light irradiation planes of the respective light emitting diodes 14 were arranged to be opposed to the outer side face at one of the circular ends of the columnar shape of the (irradiation distance-variable) photochemical reactor 11. The heat sink was indirectly cooled down with the external flow of water. The temperature of the cooling water was set to 10° C.

The method adopted for light irradiation with light emitting diodes irradiated the photoreaction liquid with light going from outside of the photochemical reactor 11 through the outer glass wall of the cylindrical end face (circular end) of the photochemical reactor 11. Thirty light emitting diodes were connected in series on one line, and three lines were arranged parallel to one another and were driven to emit light by a set of DC power source unit. The average drive current per each light emitting diode was 0.35 A/piece, and the overall input power to all the light emitting diodes was about 85 W.

A total of six liters of cyclohexane (special grade chemical, manufactured by Katayama Chemical Industries Co., Ltd.)

was provided in the photochemical reactor 11 and the separator 24 via the material supply line 25, and the reaction temperature was maintained at 20° C. Hydrogen chloride gas (manufactured by Tsurumi Soda Co., Ltd.) and nitrosyl chloride gas (obtained by synthetic reaction of nitrosylsulfuric acid and hydrogen chloride and subsequent distillation and purification) were supplied to the separator 24 respectively at a flow rate of 200 ml/min and at a flow rate of 50 to 300 ml/min to be continuously injected via the nitrosyl chloride injection line 21 into the lower part of the separator 24. The hydrogen chloride gas and the nitrosyl chloride gas were then circulated at the rate of 10 ml/min between the photochemical reactor 11 and the separator 24. Cyclohexane was accordingly exposed to the nitrosyl chloride gas in the separator 24 and was fed to the photochemical reactor 11 via the reactor input material circulation line 15. The reaction liquid was extracted from the separator 24 at the intervals of every 30 minutes after the start of the injection and was dispersed in a methanol solution of potassium iodide to produce iodine. The concentration of chloride nitrosyl was then measured with an aqueous solution of sodium thiosulfate by oxidation-reduction titration.

When the reaction started, the reaction product was accumulated in the form of oily product on the bottom of the photochemical reactor 11. The oily product on the bottom, which was protected from direct light irradiation, was extracted with the unreacted substance via the reaction liquid circulation line 16 by the reaction liquid circulation line pump 18 shown in FIG. 4 and was separated in the separator 24 by the specific gravity difference. The separated oily product was extracted via the oily product extraction line 23 at regular intervals. After the test, the total mass of the extracted oily product was measured.

The temperature of the liquid extracted by the pump from the photochemical reactor 11 via the reaction liquid circulation line 16 was measured as the temperature of the photochemical liquid. When the electric discharge lamp is used as the light source, it is required to cool down the light irradiation plane due to the heat generated by the electric discharge lamp. The light emitting diodes 1, however, have extremely low heat generation on the light irradiation plane and accordingly do not require cooling on the light irradiation planes.

The light emitting diodes 14 were then lit up to start the reaction. Only the oily product contained in the reaction liquid fed to the separator was accumulated in the separator 24 by the specific gravity difference, while unreacted cyclohexane was exposed to nitrosyl chloride and was fed again to the photochemical reactor 11.

The exhaust gas was discharged from the nitrosyl chloride-unreacted gas discharge line 22 and was absorbed into water in a scrubber. The absorbed liquid was neutralized with soda ash.

For the purpose of stable measurement, evaluation was performed for the oily product extracted at the time of 120 minutes to 180 minutes after the start of lighting of the light emitting diodes.

After the extracted oily product was dissolved in an ethanol solution and neutralized with sodium bicarbonate power, the amounts of cyclohexanone oxime and impurity were measured by GC analysis (GC-14B manufactured by Shimadzu Corporation). The concentration (percent by mass) of cyclohexanone oxime was determined from the calibration curve of GC analysis. The amount (g) of cyclohexanone oxime obtained by the reaction was calculated from the mass (g) of the oil product and converted to the molar value according to the requirements. The conditions of GC analysis were: 7% Thermon-3000 used as the stationary phase liquid; 80 to 100 meshes of Chromosorb W-AW (DMCS) used as the stationary phase carrier; the glass column of 2.1 m in length and 3.2 mm in inner bore; nitrogen gas at the rate of 25 ml/minute used as the carrier gas; the temperature of the thermostat for the column at 180° C. and the temperature of the inlet at 240° C.; FID used as the detector; and diphynyl ether used as the internal standard material.

The yield (g/kWh) of cyclohexanone oxime was calculated as the amount (g) of cyclohexanone oxime produced relative to the input power (kWh) per hour.

Example 1

The reactor having the irradiation distance (i.e. the cylinder length) of 22.5 cm was used for the reaction, with using light emitting diodes Red Orange LXML-PH01-0050 (energy conversion efficiency of 20%) manufactured by Philips Lumileds Lighting Company as the light emitting diodes for irradiation. The amount of nitrosyl chloride injected into the separator was adjusted. The measured concentration of nitrosyl chloride contained in the reaction liquid after 120 minutes to 180 minutes was 0.3 mol %. The other conditions followed the fundamental procedure described above. The results of the measurement are shown in Table 1.

Example 2

The reactor having the irradiation distance of 45 cm was used for the reaction. The amount of nitrosyl chloride injected into the separator was adjusted. The measured concentration of nitrosyl chloride contained in the liquid after 120 minutes to 180 minutes was 0.3 mol %. The other conditions were identical with those of Example 1. The results of the measurement are shown in Table 1.

Example 3

The reactor having the irradiation distance of 22.5 cm was used for the reaction, with changing the light emitting diodes for irradiation to light emitting diodes Red Orange XPERD0-1-0000-00701 (energy conversion efficiency of 35%) manufactured by Cree, Inc. The amount of nitrosyl chloride injected into the separator was adjusted. The measured concentration of nitrosyl chloride contained in the liquid after 120 minutes to 180 minutes was 0.4 mol %. The other conditions followed the fundamental procedure described above and the description of Table 1. The results of the measurement are shown in Table 1.

Example 4

The reactor having the irradiation distance of 45 cm was used for the reaction. The amount of nitrosyl chloride injected into the separator was adjusted. The measured concentration of nitrosyl chloride contained in the liquid after 120 minutes to 180 minutes was 0.4 mol %. The other conditions were identical with those of Example 3. The results of the measurement are shown in Table 1.

Comparative Examples 1 and 2

The reactor having the irradiation distance of 9 cm was used for the reaction, with using light emitting diodes Red Orange LXML-PH01-0050 (energy conversion efficiency of 20%) manufactured by Philips Lumileds Lighting Company as the light emitting diodes for irradiation. The amount of nitrosyl chloride injected into the separator was adjusted. The measured concentrations of nitrosyl chloride contained in the respective liquids after 120 minutes to 180 minutes were respectively 0.3 mol % and 0.6 mol % as shown in Table 1. The other conditions followed the fundamental procedure described above and the description of Table 1. The results of the measurement are shown in Table 1.

Comparative Examples 3 and 4

The reactor having the irradiation distance L of 22.5 cm was used for the reaction. The reaction conditions were identical with those of Comparative Example 1 described above, except that the amount of nitrosyl chloride injected into the separator was adjusted such that the concentrations of nitrosyl chloride contained in the respective liquids after 120 minutes to 180 minutes were respectively controlled to 0.6 mol % and 0.9 mol %. The results of the measurement are shown in Table 1.

Comparative Examples 5 and 6

The reactor having the irradiation distance of 45 cm was used for the reaction. The reaction conditions followed the fundamental procedure described above and the description of Table 1, except that the amount of nitrosyl chloride injected into the separator was adjusted such that the concentrations of nitrosyl chloride contained in the respective liquids after 120 minutes to 180 minutes were respectively controlled to 0.6 mol % and 0.9 mol %. The results of the measurement are shown in Table 1.

Comparative Example 7

The reactor having the irradiation distance L of 4.5 cm was used for the reaction, with changing the light emitting diodes for irradiation to light emitting diodes Cool White LXML-PWC1-0050 (energy conversion efficiency of 20%) manufactured by Philips Lumileds Lighting Company. The reaction conditions followed the fundamental procedure described above and the description of Table 1, except that the amount of nitrosyl chloride injected into the separator was adjusted such that the concentration of nitrosyl chloride contained in the liquid after 120 minutes to 180 minutes was controlled to 0.4 mol %. The results of the measurement are shown in Table 1.

Comparative Example 8

The reactor having the irradiation distance L of 4.5 cm was used for the reaction, with changing the light emitting diodes for irradiation to light emitting diodes Red LXML-PD01-0040 (energy conversion efficiency of 20%) manufactured by Philips Lumileds Lighting Company. The reaction conditions followed the fundamental procedure described above and the description of Table 1, except that the amount of nitrosyl chloride injected into the separator was adjusted such that the concentration of nitrosyl chloride contained in the liquid after 120 minutes to 180 minutes was controlled to 0.4 mol %. The results of the measurement are shown in Table 1.

TABLE 1

| | Energy Conversion Efficiency % | Dominant Wavelength nm | Wavelength Range Outputting 5% Strength of Emax nm | Irradiation Distance mm | Concentration of Nitrosyl Chloride in Liquid mol % | Yield of Cyclohexanone Oxime g/kwh | Selection Rate of Cyclohexanone Oxime % |
|---|---|---|---|---|---|---|---|
| | | | | | Reaction Condition | Results of Reaction | |
| Ex 1 | 20 | 615 | 75 | 225 | 0.3 | 140 | 80.8 |
| Ex 2 | 20 | 615 | 75 | 450 | 0.3 | 153 | 79.0 |
| Ex 3 | 35 | 615 | 75 | 225 | 0.4 | 460 | 82.8 |
| Ex 4 | 35 | 615 | 75 | 450 | 0.4 | 419 | 79.2 |
| Comp. Ex 1 | 20 | 615 | 75 | 90 | 0.3 | 100 | 80.1 |
| Comp. Ex 2 | 20 | 615 | 75 | 90 | 0.6 | 115 | 78.5 |
| Comp. Ex 3 | 20 | 615 | 75 | 225 | 0.6 | 121 | 73.6 |
| Comp. Ex 4 | 20 | 615 | 75 | 225 | 0.9 | 92 | 65.5 |
| Comp. Ex 5 | 20 | 615 | 75 | 450 | 0.6 | 97 | 68.3 |
| Comp. Ex 6 | 20 | 615 | 75 | 450 | 0.9 | 47 | 47.7 |
| Comp. Ex 7 | 20 | 443 | 275 | 45 | 0.4 | 100 | — |
| Comp. Ex 8 | 20 | 625 | 75 | 45 | 0.4 | 139 | — |

In Examples 1 to 4 satisfying the conditions that the concentration of nitrosyl chloride was 0.1 to 0.5% and that the irradiation distance was equal to or greater than 200 mm, the yields of cyclohexanone oxime were higher than those of Comparative Examples. The selection rates were also as high as 79.0 to 82.8%. In Examples 3 and 4 satisfying the conditions that the concentration of nitrosyl chloride was 0.35 to 0.5% and that the irradiation distance was equal to or greater than 200 mm, the yields of cyclohexanone oxime were higher than those of Examples 1 and 2.

Comparative Example 1 had the concentration of nitrosyl chloride in the liquid equal to 0.3%, but had the irradiation distance of 90 mm that was less than those of Examples 1 to 4. As a result, Comparative Example 1 had the selection rate of cyclohexanone oxime equivalent to those of Examples 1 to 4 but had the lower yield of cyclohexanone oxime.

Comparative Example 2 had the concentration of nitrosyl chloride in the liquid equal to 0.6% that was higher than those of Examples 1 to 4, and had the irradiation distance that was less than those of Examples 1 to 4. Comparative Example 2 accordingly had the lower yield of oxime and the lower selection rate of cyclohexanone oxime than those of Examples 1 to 4.

Comparative Examples 3 and 4 had the irradiation distance of 225 mm but had the higher concentrations (0.6% and 0.9%) of nitrosyl chloride in the liquid than those of Examples 1 to 4. As a result, Comparative Examples 3 and 4 had the lower yields of cyclohexanone oxime and the lower selection rates of cyclohexanone oxime than those of Examples 1 to 4.

Comparative Examples 5 and 6 had the further longer irradiation distance. Comparative Example 5 had the lower yield of cyclohexanone oxime and the lower selection rate of cyclohexanone oxime than those of Comparative Example 3 having the same concentration of chloride nitrosyl as that of Comparative Example 5. Similarly, Comparative Example 6 had the lower yield of cyclohexanone oxime and the lower selection rate of cyclohexanone oxime than those of Comparative Example 4 having the same concentration of chloride nitrosyl as that of Comparative Example 6.

Comparative Examples 7 and 8 had the irradiation distance of 45 mm that was less than those of Examples 1 to 4. Comparative Examples 7 and 8 had the lower yields of oxime than those of Examples 1 to 4.

According to the results described above, the optimum reaction results were obtained with respect to both the yield of cyclohexanone oxime and the selection rate of cyclohexanone oxime under the conditions that the concentration of nitrosyl chloride was 0.1 to 0.5% and that the irradiation distance was equal to or greater than 200 mm.

INDUSTRIAL APPLICABILITY

The photochemical reaction or more specifically photonitrosation is enabled with light having the emission energy distribution that is typically achievable by the light emitting diodes, which are expected as the light source for the next generation, because of the efficient use of energy and the long life. The applicability to the photochemical reaction results in expanding the use of the light emitting diodes. Additionally, application of the light emitting diodes to production by the photochemical reaction (for example, production of caprolactam or lauryl lactam or more specifically production of caprolactam from cyclohexanone oxime by photonitrosation, although the application range of the production by the photochemical reaction is not limited to such examples) allows the efficient use of emission energy for photonitrosation and enables reduction of the environmental load, energy-saving and extension of life, which may lead to significant cost reduction.

The invention claimed is:

1. A method of producing a cycloalkanone oxime comprising photochemically reacting a cycloalkane with a photo nitrosating agent in a liquid by light irradiation with a light source configured to emit light satisfying conditions that, in an emission energy distribution with respect to wavelength of light, a wavelength at which emission energy has a maximum value of 550 nm to 700 nm and a continuous wavelength range including the wavelength at which the emission energy has a maximum value and outputting energy of or over 5% strength of the maximum value is equal to or less than 150 nm, wherein an irradiation distance in the liquid is equal to or greater than 200 mm, concentration of the photo nitrosating agent in the liquid is 0.1 mol % to 0.5 mol %, and the light source is a light emitting diode and has an energy conversion efficiency equal to or greater than 10%, wherein the energy conversion efficiency is an integrated value of emission energy in a wavelength range of 400 to 780 nm with respect to an input electric power per each light emitting diode.

2. The method according to claim 1, wherein the light source has an energy conversion efficiency equal to or greater than 20%.

3. The method according to claim 1, wherein the wavelength at which the emission energy has the maximum value is 600 nm to 650 nm.

4. The method according to claim 1, wherein
the cycloalkane is cyclohexane or cyclododecane; and
the cycloalkanone oxime is cyclohexanone oxime or cyclododecanone oxime.

5. The method according to claim 1, wherein the photo nitrosating agent is nitrosyl chloride or trichloronitrosomethane.

6. A method of producing a lactam comprising reacting the cycloalkanone oxime produced by the method according to claim 1.

* * * * *